United States Patent [19]
Choudhary et al.

[11] Patent Number: 6,107,038
[45] Date of Patent: Aug. 22, 2000

[54] METHOD OF BINDING A PLURALITY OF CHEMICALS ON A SUBSTRATE BY ELECTROPHORETIC SELF-ASSEMBLY

[75] Inventors: Gargi Choudhary, Santa Clara; Karen Hahnenberger, Cupertino; Philip J. Kuekes, Menlo Park; Kay Lichtenwalter, San Jose; William S. Hancock, Hillsborough, all of Calif.

[73] Assignee: Agilent Technologies Inc., Palo Alto, Calif.

[21] Appl. No.: 09/134,855

[22] Filed: Aug. 14, 1998

[51] Int. Cl.$^7$ .................................................. C12Q 1/68
[52] U.S. Cl. ............................. 435/6; 435/288.6; 436/94; 204/450; 536/25.4
[58] Field of Search ......................... 536/25.4; 530/412, 530/344; 204/450; 422/59, 68.1, 101; 435/288.6, 6; 436/94

[56] References Cited

U.S. PATENT DOCUMENTS

| | | | |
|---|---|---|---|
| 5,532,128 | 7/1996 | Eggers et al. | 435/16 |
| 5,587,128 | 12/1996 | Wilding et al. | 422/50 |
| 5,804,384 | 9/1998 | Muller et al. | 435/6 |
| 5,843,767 | 12/1998 | Beattie | 435/287.1 |
| 5,846,727 | 12/1998 | Soper et al. | 435/6 |
| 5,922,591 | 7/1999 | Anderson et al. | 435/287.2 |

FOREIGN PATENT DOCUMENTS

98/29736  7/1998  WIPO.

*Primary Examiner*—Kenneth R. Horlick

[57] ABSTRACT

An electrophoretic technique is provided for moving a plurality of chemicals into distinct zones for immobilization on a solid surface. The technique includes introducing a first electrolyte and a second electrolyte into a channel, and interposing between the first and second electrolytes at least one solution containing a plurality of chemicals. Under a given electric field, the first electrolyte has anions with higher effective mobility than the chemicals and the second electrolyte has anions with lower effective mobility than the chemicals. When an electrical potential is applied across the length of the channel the plurality of chemicals in the solution are moved into spatial zones. The chemicals in the zones can then be bound to the interior surface of the channel. Chemicals so bound to the wall surface can be used to build very small structures such as arrays and electrical conducting structures.

40 Claims, 2 Drawing Sheets

```
                      SEQUENCE LISTING

<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<221> NAME/KEY: modified_base
<222> LOCATION: (1)
<220> FEATURE:
<221> NAME/KEY: modified_base
<222> LOCATION: (1)
<223> OTHER INFORMATION: n is 2' fluorodeoxycytidine
<220> FEATURE:
<223> OTHER INFORMATION: Description of Artificial Sequence: unknown

<400> SEQUENCE: 1
natgcatgca tgcat                                                15

<210> SEQ ID NO 2
<211> LENGTH: 14
<212> TYPE: DNA
<213> ORGANISM: Artificial Sequence
<220> FEATURE:
<221> NAME/KEY: modified_base
<222> LOCATION: (1)..(2)
<223> OTHER INFORMATION: n is 2' fluorodeoxycytidine
<220> FEATURE:
<223> OTHER INFORMATION: Description of Artificial Sequence: unknown

<400> SEQUENCE: 2
nntcacgagc gctg                                                 14

<210> SEQ ID NO 3
<211> LENGTH: 14
<212> TYPE: DNA
<213> ORGANISM: Artificial Sequence
<220> FEATURE:
<221> NAME/KEY: modified_base
<222> LOCATION: (1)..(3)
<223> OTHER INFORMATION: n is 2' fluorodeoxycytidine
<220> FEATURE:
```

```
<223> OTHER INFORMATION: Description of Artificial Sequence: unknown

<400> SEQUENCE: 3
nnnattggcc agtc                                                  14

<210> SEQ ID NO 4
<211> LENGTH: 15
<212> TYPE: DNA
<213> ORGANISM: Artificial Sequence
<220> FEATURE:
<221> NAME/KEY: modified_base
<222> LOCATION: (1)..(4)
<223> OTHER INFORMATION: n is 2' fluorodeoxycytidine
<220> FEATURE:
<223> OTHER INFORMATION: Description of Artificial Sequence: unknown

<400> SEQUENCE: 4
nnnnggccaa ttgtc                                                 15

<210> SEQ ID NO 5
<211> LENGTH: 15
<212> TYPE: DNA
<213> ORGANISM: Artificial Sequence
<220> FEATURE:
<221> NAME/KEY: modified_base
<222> LOCATION: (1)..(5)
<223> OTHER INFORMATION: n is 2' fluorodeoxycytidine
<220> FEATURE:
<223> OTHER INFORMATION: Description of Artificial Sequence: unknown

<400> SEQUENCE: 5
nnnnntactg attaa                                                 15
```

METHOD OF BINDING A PLURALITY OF CHEMICALS ON A SUBSTRATE BY ELECTROPHORETIC SELF-ASSEMBLY

FIELD OF THE INVENTION

The present invention is related to techniques for binding chemicals to a surface, and more particularly, to techniques for binding a plurality of chemicals to a surface on which the binding sites are microscopically precisely controlled.

BACKGROUND

Capillary electrophoresis (CE) is an analytical separation technique that employs a high voltage drop across a capillary column (e.g., of fused silica) which is about 5 to 100 microns ($\mu$m) in inner diameter. CE offers high speed, good resolution and efficiency that are inherent in electrokinetic separation techniques. Since CE is a liquid phase system typically containing more than 90% of aqueous phase at neutral pH, another advantage of CE is that the structural conformation of the biomolecules can be maintained. The maintenance of structural conformation has further utility in the ease of changing the environment to cause structural alterations, which in turn can create a switching device such as in the case of a pH or organic solvent or a temperature change. CE lends itself to micromanipulations. Typical injection volumes in CE are 2 to 10 nanoliters (nL) and may contain analytes as little as 100 attomole to 1 femtomole. A general reference on capillary electrophoresis is the *Handbook of Capillary Electrophoresis* edited by James P. Landers (CRC Press, Ann Arbor, 1994).

Recently, much effort has been devoted to attaching biomolecules to the surface of a substrate. One application of such effort is in creating biomolecular arrays for detection of chemicals. For example, Fodor, et al., "Light-directed, Spatially Addressable Parallel Chemical Synthesis," *Science,* Vol. 251, 767–773 (1991) disclose high-density arrays formed by light-directed synthesis. Such arrays can be used for antibody recognition. Biomolecular arrays are also described by E. Southern (PCT Publication WO 89/10977) for analyzing polynucleotide sequences. Such biomolecular arrays lend themselves to a large number of applications, from DNA and protein sequencing to DNA fingerprinting and disease diagnosis. Techniques for synthesizing a polymer array on an optical substrate are described by Fodor et al. (1991) supra; PCT publications WO 91/07087, WO 92/10587, WO 92/10588; and U.S. Pat. No. 5,143,854. The techniques of attaching chemicals to substrates and to one another in the aforementioned documents are incorporated by reference herein.

Today, however, positioning a large number of different chemicals, such as biomolecules, on a substrate in distinct locations is a difficult task. Typically, present day processes involve synthesizing an array of different ligands onto a substrate using photolithographic techniques. Such technology has serious disadvantages for the microfabrication of a large number of very small features, such as biochemical arrays. The process of photolithography is expensive and not suitable for mass production. Current technology cannot produce features of sufficiently small size, e.g., 1 micron or less. What is needed is an effective technique for arranging at different locations on a substrate a large number of different chemicals that are to be affixed on the substrate.

SUMMARY

In the present invention, electrophoretic techniques can be used to move a plurality of chemicals into distinct zones for immobilizing on a solid surface. In one aspect, the present invention provides a method for binding a plurality of chemicals on a wall surface of a channel. The method includes introducing a first electrolyte and a second electrolyte into the channel, and interposing between the first and second electrolyte at least one solution having the plurality of chemicals. Under a given electric field, the first electrolyte has anions with higher effective mobility than the chemicals, and the second electrolyte has anions with lower effective mobility than the chemicals. Applying an electrical potential difference between the two ends of the channel separates the plurality of chemicals in the solution into spatial zones; and the chemicals are then bound to the wall surface after the zones have achieved a steady state speed of migration in the channel. Alternately, ionic species as concentrated solutions or in non-liquid form, such as salts and acids, can be added into one or more solutions having the plurality of chemicals to provide the anions with lower and higher effective mobility than the chemicals.

In another aspect, in a method provided by the present invention for positioning a plurality of desired chemicals in ordered positions on a solid surface, chemicals to be so positioned are bound to affinity moieties, each having affinity for its specific counterpart chemical, thus forming targeting chemicals. Into the channel is introduced a first electrolyte, a second electrolyte, and at least one solution, which has a plurality of the counterpart chemicals to the desired chemicals, interposing between the first and the second electrolytes, wherein under a given electric field the first electrolyte has anions with higher effective mobility than the counterpart chemicals, and the second electrolyte has anions with lower effective mobility than the counterpart chemicals. Upon applying an electrical potential difference between the two ends of the channel the plurality of counterpart chemicals in the solution are separated into spatial zones. The counterpart chemicals are then bound to the wall surface after the zones have achieved a steady state speed of migration in the channel. The targeting chemicals are then bound to the plurality of counterpart chemicals. Again, in an alternative, the electrolytes can be replaced with ionic species in solid form or as concentrates.

In yet another aspect, because of the unique technique for arranging a plurality of chemicals along a channel, the present invention provides a device for anchoring a plurality of target molecular structures. The device includes a channel having channel walls, the channel walls having a series of hundreds or more of zones along the channel, each zone having a different binder chemical for binding counterpart molecules.

As used herein, the term "complement" and "complementarity" refer to a biomolecule, e.g., oligonucleotide, hybridizing or mating with other biomolecule(s) to form a matched duplex or triplex. "Complementarity" includes the matching up and the mutual adaptation of surfaces of two macromolecules, such as in antigen-antibody binding (pairing), nucleic acid sequences annealing (pairing), protein-receptor binding (pairing), polysaccharides pairing, polypeptides pairing, and the like. As used herein, a single stranded biomolecule may complement a double stranded biomolecule and vice versa to form a triplex. (See, for example, J. C. Francois, T. Saison-Bchmoaras, N. T. Thuong, C. Helenc, *Biochemistry,* 28:9617–9619 (1989).) An example of a complement is an oligonucleotide hybridizing with another oligonucleotide by hydrogen bonding between the bases (e.g., to form a double helical structure) wherein adenine (A) is matched with thymine (T), guanine (G) is matched with cytosine, and uracil (U) is matched with adenine (A). The term "oligonucleotide" includes linear oligomers of natural or modified monomers or linkages including deoxyribose nucleosides, ribose nucleosides, α-anomeric forms thereof, peptides, nucleic acids, peptide-nucleic acids (PNA), aptamers, or the like, capable of binding to a target polynucleotide by regular pattern of interaction, such as Watson-Crick type base pairing, base stacking, Hoogsteen or reverse Hoogsteen types of base-pairing, and the like, involving specific hydrogen bonding interactions. "Biomolecules" refer to polymers or oligomers of natural or modified monomers of nucleosides, nucleic acids, peptides, peptoids (which are protein analogs, see, e.g., *Proc. Natl. Acad. Sci. USA*, 95, 4303 (1998)), saccharides, fatty acids, and the like, so long as the polymers or oligomers of the modified monomers have the ability to complement molecules of similar nature in a similar way to the natural polymers or oligomers.

The present invention uses isotachophoresis or related focusing technologies in the construction of a pattern of location of different chemicals on a substrate. With the present technique, unlike prior techniques, there is no need to individually and separately position and affix different chemicals on specific sites on the substrate in a temporally serial manner. The present technique allows a plurality of different chemicals to arrange among themselves under an electric field before affixing to the solid surface. Thus, this technique is referred to as "self-assembly." Further, the different chemicals arrange by themselves substantially simultaneously, in a temporally parallel fashion. In another aspect, the present technique is capable of "self-assembly" in that complementary chemicals, such as complementary DNA strands, protein-antibody pairs, and the like, seek out their complementary counterparts due to the affinity of a chemical for its complementary counterpart.

The technique is based on isotachophoresis to focus/localize binder chemicals, such as synthetic oligonucleotides, which are then chemically bound to the surface of the substrate. Upon applying an electric field to a discontinuous buffer system oligonucleotides can be localized to zones that are as small as 0.1–1 $\mu$m in width. Such small zones of chemical concentration are not currently possible with the current photolithographic techniques used in DNA array formation. The isotachophoresis technique of the present invention affords the advantage of making a large number of very small zones of different chemicals on the substrate. Such patterns of small zones can be advantageously used for forming a wide variety of useful products, such as a biomolecule array for testing genetic DNA materials, forming memory for computing, and as an assembler for biomolecule scaffolding to be used as a platform for molecular wires and nano-structures, DNA computational algorithms and assembly of quantum dot structures.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

In one aspect, the present invention provides a technique for binding a large number of different chemicals on a solid surface, particularly in such a way to enable identifying the location of these chemicals on the solid surface. To this end, a large number of binder chemicals (e.g., each having a biomolecule such as DNA sequence), each having an affinity for a specific chemical moiety (e.g., each having a biomolecule such as DNA sequence) that is desired to be affixed to the solid surface, is localized by isotachophoresis and affixed to the solid surface. Then targeting chemicals, which contains the specific chemical moieties of interest, are bound to the binder chemicals selectively by the affinity of the targeting chemicals for the binder chemicals.

Separation of Binder Chemicals on the Solid Surface Before Binding

The binder chemicals are separated, by isotachophoresis, according to their respective effective mobility under an electric field on the solid surface before the binder chemicals are anchored (i.e., bound or affixed) to the solid surface.

In an applied electric field (E), ions with an effective mobility of ($\mu$) will move with a velocity (V) with a relation of:

$$V = \mu E$$

The effective mobility of an ion depends on factors such as the pH, temperature, viscosity of the media in which the ion moves.

Figure 1:
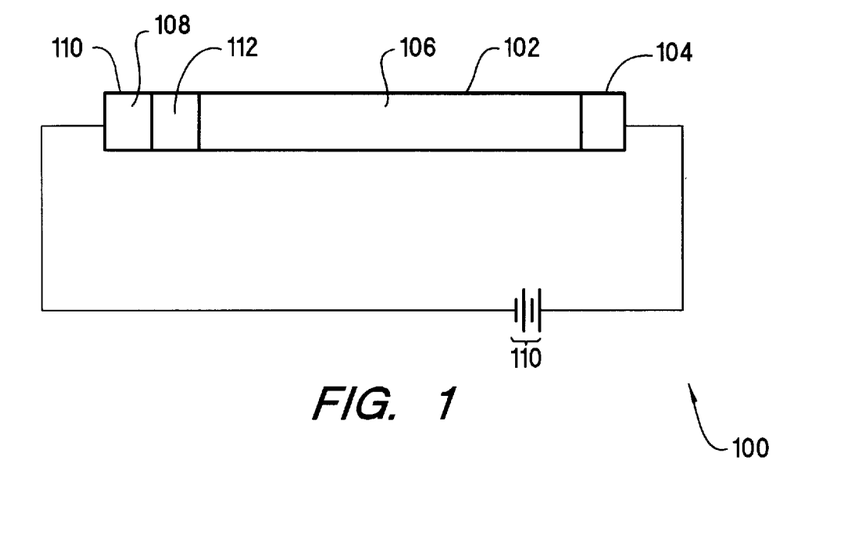
FIG. 1 shows in schematic representation of an embodiment of an apparatus according to the present invention for positioning binder chemical in desired locations.

To separate a number of ions of interest (the "sample ions," which contain the binder chemicals), a sample solution containing the sample ions is sandwiched between a leading electrolyte with ions having higher effective mobility than the ions of interest and a terminating electrolyte with ions having lower effective mobility than the ions of interest. For example, FIG. 1 depicts an apparatus 100 of the present invention for positioning binder chemicals in desired locations. For example, to separate a number of sample anions (which contain binder chemicals), a channel 102, such as a capillary, as well as an anode compartment 104 connected to it, are filled with an electrolyte, the "leading electrolyte" 106. The anions in the leading electrolyte 106 have a higher effective mobility than any of the sample anions. A terminating electrolyte 108 is placed at a cathode compartment 110. The anions of the terminating electrolyte 108 have an effective mobility lower than any of sample anions. A sample solution 112 containing the sample ions is injected between the leading electrolyte 106 and the terminating electrolyte 110.

Figure 2:
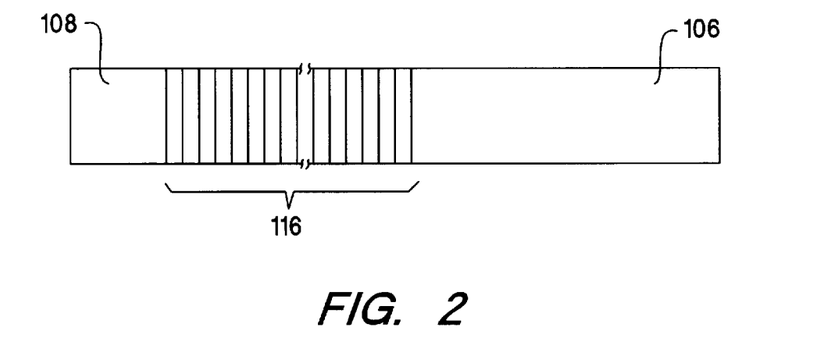
FIG. 2 depicts a schematic representation of an embodiment of a channel containing the zones of electrolytes and chemicals.

Passing electrical current through the capillary between the anode and cathode, for example, by connecting to a voltage supply 110 to impose an electrical potential difference, will apply an electric field across the electrolytes and the ions. The anions with the highest effective mobility will migrate with the highest velocity whereas those having the lowest effective mobility will migrate with the lowest velocity towards the anode. In time, the different anions in the sample solution 112 will separate into distinct zones in order of their effective mobility. Each zone contains one species of anion, with the leading zone containing the leading anions of the leading electrolyte and the terminating zone containing the terminating anions of the terminating electrolyte. A steady state will be reached at which the zones migrate at the same velocity, connected together in series. When the zones approach travelling at the same speed, they are substantially pure. FIG. 2 depicts a schematic representation of a channel 102 containing the zone of leading electrolyte 106, the zone of the terminating electrolyte 108, and a plurality of zones 116 of ions of binder chemicals in between. Very narrow zones can be achieved because if an anion moves ahead approaching the zone in front of it that anion experiences an electric field that tends to slow it down, whereas if the anion falls back approaching the zone that follows it, the opposite is true. Similarly, isotachophoresis can be conducted to separated zones of positively charged ions.

Standard equipment for conducting traditional isotachophoresis and electrophoresis can be used for the above-described separation of ions. Methods and apparatuses for isotachophoresis and electrophoresis are known in the art. For example, use of isotachophoresis in separation of amino acids and peptides has been described by Everaerts, et al., in "Isotachophoresis: theory, instrumentation and application," *J. Of Chromatography Libr.,* Vol 6, p301–336 (1976), and Kasicka, et al. "Isotachophoretic analysis of peptides: Selection of electrolyte systems and determination of purity," *J. Chromatogr.,* 470:209–221 (1989). Isotachophoresis of proteins is described, for example, by Stover, et al., "Spacer performance in cationic isotachophoresis of proteins," *J. Chromatogr.,* 470:, 201–208 (1989). Use of Isotachophoresis of nucleotides is described, for example, by Everaerts, et al. ; and in "Isotachophoresis: theory, instrumentation and application," *J. Of Chromatography Libr.,* Vol 6, p337–342 (1976). A model G1600 AX HP 3D capillary electrophoresis unit (Hewlett Packard Co, Palo Alto, Calif.) can be adapted for performing capillary isotachophoresis. The methods for isotachophoresis on a wide range of compounds are described, for example, in "Isotachophoresis: theory, instrumentation and application," *J. Chromatography Libr.,* 1976, Vol 6, *High resolution separation and analysis of biological macromolecules, Part A fundamentals,* edited by B. Karger and W. S. Hancock, vol. 270 1996, 375–400.

Generally, the appropriate conditions for conducting isotachophoresis are such that the oligomer molecules have differences that affect the effective mobility. For example, there may be a difference in electrical charge at the end of the oligomers, such as in the form of difference in modified bases. See, for example, N. Bischofberger, M. D. Matteucci, *J. Am. Chem. Soc.,* 1989, 111, 3041–3046 talks about novel polycyclic nucleoside analogues and their incorporation into the DNA sequence. Other examples include 2'-Hydroxyl or 2'-fluoro deoxycytidine, or deoxyadenosine or deoxyguanosine or deoxyuridine. See, e.g., W. Tang, L. Zhu, L. Smith, *Anal. Chem.,* 1997, 69, 302–312. For example, a mixture may contain ATCG(MB+1)T, ATCG(MB+2)T, ATCG(MB+3)T, where MB+1, MB+2, and MB+3 represent modified base with one electrical charge, two electrical charges, and three electrical charges, respectively. Using this technique, oligomers of the same length can be separated by isotachophoresis. In some cases, the oligomers of the same length can be separated if they have a region with different base composition. For example, a mixture containing ATCGT, ACCGT, ACCCT, and ATCCT, due to their differences in pKa values, can be separated from one other by isotachophoresis at pH of about 4 to 5. By selecting nucleic acid sequences with differences in bases, and if desired, modifying them with different number of electrical charges, one will be able to make a vast number of molecules that can be readily separated by isotachophoresis under appropriate pH.

Another type of oligomers that can be separated by isotachophoresis include hybrids, such as hybrid peptide-DNA structures with charge difference or length difference, controlled by the peptide or hybrid carbohydrate-DNA structure with charge difference controlled by different number of sialic acid groups on the carbohydrates.

For separation into zones of chemicals for affixing to the surface of the channel, the channel diameter for performing isotachophoresis can range from 1–500 $\mu$m. The range is preferably 5–300 $\mu$m, more preferably 50–200 $\mu$m due to the ease of working with such a size and the large number of channels that can be placed in close proximity. Generally, commercially available power supplies and equipment can be used for isotachophoresis on such channels. The applied voltage ranges from 0–30 kV for commercially available instruments.

As stated previously, capillary electrophoresis, as does isotachophoresis, can separate biomolecules by virtue of the difference in their mobility. The mobility is represented by the ratio of charge(z) to hydrodynamic radius (r) (size) as $$\mu = z/6\pi\eta r$$

where $\eta$ is the viscosity of the medium.

An example of the resolving power of capillary electrophoresis and isotachophoresis has been illustrated by its use for monitoring the deamidation of recombinant human growth hormone. In this case the peptide with two deamidation sites could be separated from that with only one deamidation site as well as the nondeamidated variant, illustrating the ability of capillary electrophoresis in resolving biomolecules with small difference in the ratio of charge to size. See, R. G. Nielsen, E. C. Rickard, "Applications of capillary zone electrophoresis to quality control," *ACS Symp. Ser.,* 434,36, (1990) for such experiments. Generally, isotachophoresis can be used to separate biomolecules with ratio of mobility difference to absolute mobility ($\Delta\mu/\mu$) of 0.01 (note no units since it is a ratio), preferably a ratio of 0.05. The range of high electrophoretic mobilities is $4\times10^{-3}$ to $1\times10^{-3}$ cm$^2$/V.sec. The range that can be considered as low electrophoretic mobilities is $4\times10^{-5}$ to $1\times10^{-5}$ cm$^2$/V.sec. Aside from published data of mobilities, it is also within the skill of a person skilled in the art to determine the relative mobilities of a wide variety of molecules by considering the type, size and charge of molecules and doing routine evaluation to compare the relative mobilities. No undue amount of experimentation will be needed. Due to the differences in molecular size, structure, and charge possible with polymers (especially biopolymers), myriads of molecules with different effective mobilities can be made.

Using the present technique of focusing molecules into zones by isotachophoresis, zones of 10 microns or less in width can easily be made. Very small zones, as small as 0.1 to 1 micron wide, can be formed with the present isotachophoresis technique. Thus, with a 10 cm long capillary, $10^5$ zones can be formed. Each such zone can contain tens of thousands of molecules. Thus, in a substrate having $10^3$ capillaries, there can be as many as $10^8$ zones, for example, containing $10^{11}$ molecules. Thus, for a capillary, 100 zones, 1,000 zones, and 10,000 zones can readily be formed with the present technique.

Binding of Binder Chemicals onto a Solid Surface

To bind a large number of binder chemicals onto a solid surface, the binder chemicals are first separated into zones each containing substantially a single species on the solid surface, for example, as in the channel described in the above. The binder chemicals are then bound onto the solid surface, for example, by reacting a functional group in the binder chemicals with a functional group on the solid surface.

biomolecule to that chemical species in the presence of ultraviolet light. Upon exposing the surface of the capillary to light at the wavelength of 300–460 nm photolysis occurs and the biomolecule can be bound to the azide group as in the following depicted chemical reaction. The nitro group on the phenyl azide shifts the optimal wavelength for photolysis to 320–350 nm, which helps to maintain the biological integrity of the biomolecules since they absorb at $\lambda$<300 nm.

Various techniques of reacting functional groups on a solid surface with a functional group of an adjacent molecule to bind the molecule to the solid surface are known in the art. As an example, the solid surface can be chemically modified to react with the binder chemicals under the right condition, e.g., by activation by light, a change in temperature, or a reaction with a chemical.

This technique involves anchoring a spacer chemical (or linker chemical) on the surface of the fused silica capillary with a physical or chemical attachment. As an illustrative example, the following chemical reactions show how a molecule can be bound to a silica surface. A linker chemical having a photoreactive azide group at one end and an epoxy group at the other end can be used to link a biomolecule (or a binder chemical that includes biomolecule) to a solid surface. The epoxy group would react with the silanol groups according to the following reaction scheme:

Thereafter, to bind a biomolecule (or binder chemical) to the linker chemical on the silica surface (i.e., the linker chemical's corresponding chemical species that remains on the silica surface after binding thereto), one can bring the

The above reaction scheme shows the most common functional groups available in the biomolecule. However, other functional groups may be involved, e.g., alkoxide (—OR), acid (—COOH), etc., are applicable for a variety of biomolecules, i.e., it can be used for binding proteins, oligonucleotides, peptoids, and carbohydrates, and the like. Other similar reaction schemes can also be chosen for binding the focused bands of biomolecules, such as DNA, to a solid surface.

Another example of binding a binder chemical to a solid surface is by treating the surface with amino propyl triethoxy silane (APTES) reagent that possess functionalities allowing chemical binding both to the surface and to the biomolecule. APTES binds to a siliceous surface via condensation of its silyl ester moieties. The amino group of APTES is subsequently protected by treatment with 2-nitrobenzyl chloroformate. Thus protected, the entire surface has now been rendered inactive. This is followed by isotachophoresis of the biomolecules. Once a steady isotachic profile is attained, the entire surface is irradiated with light regenerating the amine functionality, which then reacts with the DNA or other molecules to produce an array of surface-fixed biomolecules or binder molecules which may have biomolecules.

The following is another example of applicable chemical binding chemistry for linking the biomolecule to a solid surface. The solid surface is made to have an active acid chloride group

One end of the biomolecule, such as a DNA molecule, is protected by a trityl amino group In which the φ is a phenyl group.
A photochemical reaction is first used to deprotect the amino group.

The deprotected DNA molecule would then react with the acid chloride group at a suitable pH as An alternative to a surface having an acid chloride group is one with an azide (—CON$_3$) group. The —CON$_3$ group can also react with DNA—NH$_2$ to form the group —CONH—DNA, which is linked to the solid surface.

The above are just illustrative examples, other examples of active groups that can be used for binding biomolecules to a solid surface are known in the art. For such linking functions, a linker is typically a bifunctional reagent with one functional group available for binding to the surface and the other for reacting with a biomolecule, e.g., upon exposure to light. Examples of functional groups that would react with the silica surface include triethoxysilane, trimethoxysilane, trichlorosilane, dichlorosilane, and chlorosilane.

The groups reactive towards biomolecules include nitrophenyl azide (reactive towards amino groups of biomolecules), phenyl azide group (reactive towards amino groups of biomolecules), and amino group (reactive towards carboxyl, hydroxyl group), carboxyl (reactive towards amino groups), and thiol (reactive towards disulfides). The functional groups at the two ends of the reagent can be linked to each other by, e.g., an alkyl group in the center giving a general configuration of FnG1—R—FnG2, where R is an alkyl group, and FnG1 and FnG2 represent the two functional groups. In theory any small molecule can function as an intermediary linker between a matrix (such as a siliceous substrate) and a ligand. However most linker molecules are built from individual molecules no more than 10 atoms in length. The best choices have appropriate coupling functionalities at either end and an overall hydrophilic character. Some of the most popular linker molecules are DADPA, i.e., diaminodipropylamine. The DADPA can be coupled to a matrix with either carbonyl diimidazole activated support to give an uncharged carbamate linkage that has the active amine. This active amino group can be protected with 2-nitrobenzyl chloroformate that can subsequently be photodeprotected after isotachophoresis has been performed. Another example is 6-aminocaproic acid that can react with imidocarbonate surface to give an active carboxyl group.

Another example is ethylene diamine that can convert carboxylate terminals into amines. It is also used in the transamidination reaction of polyacrylamide to create primary amine functionalities. Further examples include succinic acid, 1,3-diamino-2-propanol. Certain amino acids can also be used as linker molecules. See, G. T. Hermanson, A. K. Mallia, P. K. Smith, *Immobilized affinity ligand techniques*, 1992, p.150.

Yet another example of applicable techniques for binding biomolecules to a solid surface is using a solid surface with multiple functional groups, e.g., triazine with three chlorines that have multiple activity at different temperatures. Radial electric fields can be used to selectively protonate or deprotonate the surface and thus act as a promoter or inhibitor of the reactions thus providing for a tunable surface (see U.S. Pat. No. 5,180,475 issued to Young et al.). In this way, the number of branches, as well as the positions of the branches, extending from a single location on the solid surface can be controlled. The above is just an illustrative example, other examples of active groups will be known to one skilled in the art.

Other techniques of binding biomolecules to a solid surface are known in the art, and such techniques can be adapted for binding linker chemicals, and subsequently biomolecules to the solid surface. For example, Pirrung, et al (U.S. Pat. No. 5,143,854) describe binding polymers such as sequences of peptides, nucleic acids, etc., onto a substrate using linker molecules. In certain embodiments, a protective group is provided to protect the linker molecules or the substrate before binding the polymers. Exposure to radiation, electric fields, electric currents, or other activators can remove the protective group. The techniques for linking and binding linker molecules and polymers to the surface of a substrate according to Pirrung et al. are incorporated by reference herein.

Figure 5:
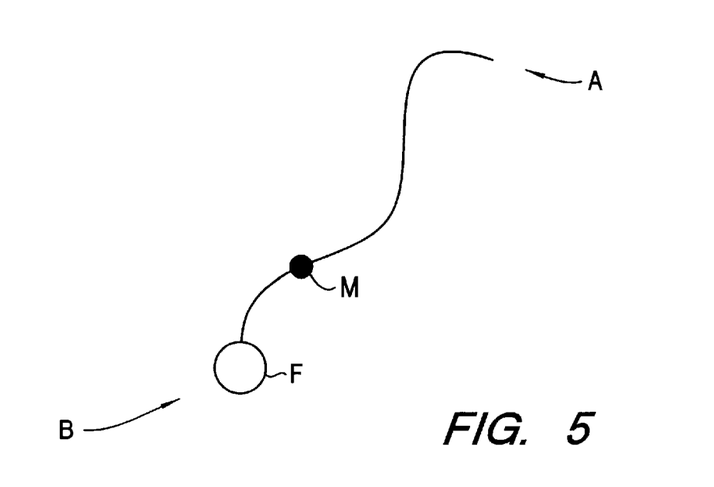
FIG. 5 shows a schematic representation of an embodiment of DNA with modified charge.

With the present technique, small amounts of biomolecules, such as oligonucleotides, can be concentrated/amplified by employing capillary isotachophoretic technique to bind to the capillary surface. Ordinarily, many biomolecules, such as oligonucleotides, cannot be separated by capillary electrophoresis by virtue of their size alone. However, synthetic biomolecules, such as synthetic DNA molecules, having the same size but differing in charge can be prepared with a distal region for hybridization and a proximal region with sufficient charge to allow effective focusing/separation. A functional group, e.g., carboxyl group, amino group, hydroxyl group, carboxyl group, thiol group are typically found on biomolecules and can also be present in the synthetic DNA for anchoring onto the surface of the capillary. These groups can be protected with a photo-deprotectable group, for example to 2-nitrobenzyl chloroformate, before the biomolecule (which may be synthetic as the term biomolecule is used herein) is positioned in a channel by isotachophoresis and subsequently deprotected by light to cause binding to the solid surface of the channel. An example of such a modified molecule is shown in FIG. 5. In FIG. 5, A represents the 3' end and B represents the 5' end of the DNA sequence. M represents the modified charge moiety and F represents the functional group for binding to the surface of the channel.

DNA molecules that have the same charge to size ratio will all get focused in the same zone. One can use techniques of molecular tomography to determine the positional identity of these molecules. Such a technique would use fluorescence detection or atomic force microscopy.

A wide variety of solid surfaces can be used for binding the linker chemicals for affixing the binder chemical. For example, the solid can be a glass, quartz, or polymeric (e.g., polydimethylsiloxane (PDMS), polyimide, polyvinyl alcohol, polystyrene, and the like. A procedure for obtaining highly stable coated capillaries for protein separation includes reaction of surface-chlorinated fused silica capillaries with Grignard reagent, vinyl magnesium bromide, followed by reaction of the vinyl group with acrylamide to produce an immobilized layer of polyacrylamide attached through hydrolytically stable Si—C bonds. See, e.g., Electrophoretic separation of proteins in capillaries with hydrolytically stable surface structures, K. Cobb, V. Dolnik, and M. Novotny, *Anal. Chem.* 1990, 2478–2483. Another example for obtaining a hydrophilic positively charged durable coating for capillary electrophoresis of macromolecules is to adsorb polyethyleneimine on to the fused silica surface and then crosslinking the adsorbed surface to give a stable layer. See, e.g., J. K. Towns, F. E. Regnier, *J. Chromatogr.* 516, 1990, 69–78. Further examples of modification of fused silica capillaries include treating the surface with γ-glycidoxypropyl-trimethoxy silane. The surface is further treated with a solution of 20% polyethylene glycol 600 and 2% boron trifluoride etherate in dioxane for 1 hour at 100° C. producing a stable wall coating for protein separations. See, e.g., G. J. M. Bruin, J. P. Chang, R. H. Kuhlman, K. Zegers, J. C. Kraak, H. Poppe, *J. Chromatogr.,* 471, 1989, 429–436. A recently developed technique involves coating capillary columns using non-ionic surfactants like TWEEN (polyoxyethylene sorbitan monoalkylates) and BRIJ (polyoxyethylene alkyl ethers) that can be hydrophobically adsorbed onto an alkylsilane-derivatized surface to create a hydrophilic layer for efficient protein separations. See, e.g., J. K. Towns, F. E. Regnier, *Anal. Chem.,* 1991, 63, 1126–1132.

An example of a reaction scheme for binding a biomolecule, for example, an antibody or a protein containing an amine group to a polymeric surface, is to first modify the protein or antibody with a crosslinker that can be photoactivated using an amine reactive end such as an N-hydroxy succinimide (NHS) ester. This would be followed by the isotachophoresis process steps. When a steady state is reached, photoreacting by exposure of the polymeric surface to strong light in the range of 320–350 nm will result in a covalently immobilized biomolecule to the surface. The photoreaction binding of the biomolecules to the channel surface will rapidly stop the further migration of the biomolecules (those that react) along the channel. An example of this approach is illustrated in the following reaction scheme using the cross linking reagent sulfosuccinimidyl-6-(4'-azido-2'-nitrophenyl-amino)-hexonate (sulfo-SANPAH)

Another example of such bifunctional groups is APDP, i.e.,(N-[4-(p-azidosalicylamido)butyl]-3'-(2'-pyridyldithio) propionamide). APDP can be first reacted with a free sulfhydryl containing biomolecules by disulfide exchange, the phenyl azide group can then be reacted photochemically with the polymeric surface. Yet other examples of such bifunctional groups include ASBA, i.e., (4-(p-Azidosalicylamido)butylamine), BASED, i.e., Bis-(β-(4-(p-Azidosalicylamido)ethyl)disulfide, sulfo SADP, i.e., sulfosuccinimidyl-(4'-azidophenyldithio)-propionate, sulfoSAMCA, i.e., sulfosuccinimidyl 7-azido-4-methylcoumarin-3-acetate, and sulfoSAPB, i.e., sulfosuccimidyl-4-(p-azidophenyl) Furthermore, the solid surface can be coated to reduce fouling by biomolecules. For example, coatings of polyvinyl alcohol (PVA), bovine serum albumin (BSA) tend to reduce biofouling. Also, the solid surface can be modified (coated) to provide a photoreactive surface such that the linker can be bound to the coated surface in a way similar to photoprotecting the linker molecules described above.

The binder molecule (containing biomolecules) can be focused into zones by isotachophoresis before attaching to the solid surface with the linker chemicals. The binder chemicals containing biomolecules, once attached to the linker chemicals on the solid surface, can be used to bind to target chemicals, which have affinity for specific binder chemicals, typically due to the three dimensional structural characteristics, such as folding of the target chemicals and the binder chemicals.

Reversible and oriented immobilization of proteins in a functionally active form on solid surface can also be achieved. Histidine tagged proteins can be reversibly immobilized on a quartz surface in an oriented manner while their function is preserved. This approach is based on immobilized metal ion affinity chromatographic technique. The surface of quartz is first activated by immersion for 1 hour in sulfuric acid with small amount of fresh ammonium peroxodisulfate added and washed. It can then be heated to 180° C. for 30 min and then silanized with 3-(mercaptopropyl)trimethoxy silane for 24 hour. The silanized surface was treated with $N^\alpha,N^\alpha$-bis-(carboxymethyl) maleimide for 1 hour and subsequently loaded with divalent metal cation e.g., $Ni^{2+}$. The free coordination sites of the chelator-metal complex are subsequently filled by additional electron-donating groups such as histidine residues. The binding of proteins to NTA is highly specific with reasonable affinities and in addition fully reversible upon addition of competitive ligand (histidine, imidazole), reprotonation of the histidine residues, or removal of the metal ion via forming a complex with EDTA. See, e.g., E. Schmid, T. A. Keller, Z. Dienes and H. Vogel, *Anal. Chem.*, 69, 1997, 1979–1985.

Targeting Chemicals that Bind to Binder Chemicals

With binder chemicals (i.e., containing biomolecules) anchored to the solid surface and each species of the binder chemicals being different and having affinity for a different target chemical, it is possible to bind different target chemicals to a different location (i.e. zone position) on the solid surface.

Various schemes of pairing can be exploited to achieve such specific affinity between the binder chemicals and target chemicals. Techniques known in the art of pairs of chemicals with specific affinity for each other can be used. For example, antigen-antibody, avidin-biotin, DNA-DNA, RNA-DNA, protein-receptor, protein-nucleic acids sequence, peptoid-DNA, polysaccharide-lectin, and the like. It is to be understood that a person skilled in the art will know that a wide variety of combinations can be used in each of such pairs and among the various pairs to achieve the binding of a large number of different target chemicals. For example, there are a wide variety of antigen-antibody pairs that can be used. Similarly, the other types of pairs (DNA, RNA, protein, peptoid, etc.) also have molecular variations that enable a large number of target chemicals to be bound to specific sites on the solid surface. For example, a large selection of affinity purified antibodies and antibodies to $F(ab')_2$ and $F_c$ immunoglobulin fragments are available, whether unconjugated or conjugated with biotin, alkaline phosphatase, horseradish peroxidase, fluorescein, rhodamine and colloidal gold. See, for example, *PIERCE products catalog*, 1997, page 77. Similarly, monoclonal antibodies with specificity to a large number of proteins, steroids and lectins, for example, apolipoprotein A-1, apolipoprotein B, cytokeratin, fibronectin, hepatitis B surface antigen, human growth hormone, thyroid stimulating hormone, cortisole, progesterone, testosterone, etc., can be found. See, e.g., *PIERCE products catalog*, 1997, page 81. Among the various antigen antibody chemistries available, antigen antibody pairing with binding constant greater than $10^{-7}$ M are more suitable for the purposes of this invention. Also, it is to be understood that many related molecules may have similar structures that can pair with the same chemical. For example, instead of avidin, similar molecules such as streptavidin and analogs of avidin can be used. Further, either adenine (A) or uracil (U) may pair with thymine (T) in nucleic acid pairing. Either natural or synthetic nucleic acid sequences can be used for pairing as the binder chemical and the target chemical. Other examples of affinity interactions and complementarity include the affinity binding of certain peptides with carbohydrates. See, e.g., Y. Konami, K. Yamamoto, T. Osawa, *J. Chromatogr.*, 597, 1992, 213–219.

A particularly useful pairing is the nucleic acid sequence to nucleic acid sequence type of binder chemical—target chemical pairing. This type of pairing affords the advantage of complementarity between the target chemicals and the binder chemicals as long as the different target chemicals of interest will each bind to only one binder chemical. Particularly useful in the present invention is the base sequence complementarity that is present in the pairing of nucleic acid sequences. Such base sequence complementarity are present in Watson-Crick base pairing, Hoogsteen base pairing, RNA-DNA pairing, DNA-PNA (PNA is protein-nucleic acid polymer) pairing, aptamer-protein pairing, triple helix formation, and the like. Such base sequence complementarity is very useful because of the large number of different sequences that can be used to afford selectivity in binding a large number of different target molecules to a substrate surface.

Yet another useful pairing can be found in the selective binding of double stranded DNA to synthetic polymers that bind to the double strand by hydrogen bonding. For example, polyimide hairpin molecules have been designed to wrap around segments of double stranded DNA and can thus recognize specific sequences. One arm of the synthetic polymer hairpin bonds with the bases in one strand and the other arm of the hairpin bonds with the other strand of the double stranded DNA. See, e.g., *Nature*, 391, 468, (1998) and *Chemical and Engineering News*, p. 7, Feb. 2, (1998), said descriptions are incorporated by reference herein. In applying these pairing, one can bind the double stranded DNA to the solid surface as the binder chemical and use the polyamide hairpins to locate the corresponding DNA strands. Yet another example of biomolecule binding for application as binder chemical and target chemical is the binding of peptoids to DNA. Peptoids are peptide analogs, which, although having no backbone hydrogen bonds, can have stable helical structures. Peptoids have been shown to bind to DNA. See, for example, *Proc. Natl. Acad. Sci. USA*, 95, 4303 (1998), *Proc. Natl. Acad. Sci. USA*, 95, 4309 (1998), and *Proc. Natl. Acad. Sci. USA*, 95, 1517 (1998), said disclosures are incorporated by reference in entirety herein. It is to be understood that when a binder chemical binds to a target chemical, the residue species of the binder chemical and the residue species of the target chemical are coupled and a leaving group or molecule may be formed.

Exemplary procedures are given below to illustrate various embodiments of the present invention, e.g., how biomolecule binder chemicals and biomolecule target chemicals are bound to a solid surface.

Procedure 1

Procedure for Treating and Activating the Surface of Fused Silica Capillary with Aminopropyltriethoxy Silane The following process can be used to activate a silica capillary surface:

1) Rinse the inner surface of fused silica capillary with 0.5 M HCl for 2 hours at room temperature.
2) Seal the ends of the capillary and heat it at 100° C. for 2 hours.
3) Rinse the capillary with deionized water for 30 minutes followed by acetone rinse for about the same amount of time.
4) Place the capillary again in an oven and purge it with nitrogen for 1 hour to remove residual water.
5) Prepare a solution containing 10% (v/v) aminopropyltriethoxy silane in toluene, deaerate with helium for 15 minutes and then fill it in the pretreated capillary.
6) Seal the ends of the capillary and place it in an oven at 120° C. for 6 hours. The capillary is then taken out and washed extensively with dimethylformamide, methanol and methylene chloride and is blown dry with nitrogen.

The above procedure can be adapted with a wide range of silanizing agents with minor modifications. The amino groups now present at the surface of the capillary can be protected by treating with 1 M solution of nitrobenzyl chloroformate.

Procedure 2

Isotachophoresis Method

After the surface of the fused silica is treated with APTES and then photoprotected with nitrobenzyl chloroformate, isotachophoresis can be performed. For positively charged biomolecules the leading electrolyte can be chosen as 0.01 M–0.05 M triethyleneamine treated to pH 3.5–4.2 with formic acid, or pH 4.2–5.2 with acetic acid. For analytes with high electrophoretic mobilities, $4\times10^{-3}$ to $1\times10^{-3}$ cm$^2$/V.sec or higher, (for example, small ions such as positively charged amino acids or dipeptides or single base nucleic acids), sodium, potassium or ammonium salts of respective acids can be used as leading electrolytes, whereas 0.1 M acetic acid can be used as the terminating electrolyte. Similarly for negatively charged biomolecules the leading electrolyte can be 0.01–0.1 M acetic acid titrated to pH 5.5–6.5 with histidine or pH 7.5–8.5 with Tris. For analytes with high electrophoretic mobilities, HCl can be used instead of acetic acid. For the terminating electrolyte, 0.01 M TAPS (N-tris[hydroxymethyl]methyl-3-aminopropane sulfonic acid can be used. In cases in which acetic acid is used as the leading electrolyte and histidine or Tris as the terminating electrolyte, such are examples for medium to low electrophoretic mobilities for negatively charged analytes.

Isotachophoresis can also be carried out in a single buffer system. There are, however, two important requirements. First the mobility of the co-ion in the buffer must be low during the isotachophoresis step so that it can serve as the terminating ion. Second, the sample must contain additional co-ion with high electrophoretic mobility, which can serve as the leading zone during isotachophoresis. Suitable salts can be added to the samples with dilute electrolyte solution to provide for optimal conditions. For example, for positively charged biomolecules either 0.01–0.1 M acetic acid or 0.01–0.1 M β-alanine+acetic acid, pH 3.5–4.3; or 0.01–0.1 M ε-aminocaproic acid+acetic acid, pH 4.1–4.8; or 0.01–0.1 M histidine+acetic acid, pH 5.5–6.3 can be used as the buffer. Sodium, potassium or ammonium acetate salts can be added to the sample. Similarly for negatively charged biomolecules, 0.01–0.1 M MES (2-[N-morpholino]ethane sulfonic acid)+histidine(or Tris) pH 5.5–6.5; or 0.01M TES (N-Tris[hydroxymethyl]methyl-2-aminoethane-sulfonic acid)+Tris, pH 7.0–8.0; or 0.01–0.1 M TAPS (N-Tris[hydroxymethyl]methyl-3-aminopropane-sulfonic acid)+Tris, pH 8.0–9.0 can be used as the buffer. Tris -acetate, sulfate or chloride ions can be added to the sample. A sample comprising of for example cytochrome c, ribonuclease A, myoglobin, carbonic anhydrase and chymotrypsinogen in the concentration of 3–5 $\mu$M can be stacked (i.e., separated into zones) by isotachophoresis on a 75 micron, 50 cm fused silica capillary at an applied voltage of about 30 kV using 0.02 M triethylene amine+acetic acid, pH 4.3 as the leading electrolyte and 0.01 M acetic acid as the terminating electrolyte. After the zones move at a constant speed the entire capillary can be exposed to light and the zones thereby bound to the surface. In another example adenosine diphosphate, adenosine triphosphate and inorganic orthophosphate can be stacked by isotachophoresis in a 400-micron i.d. and 28 cm long capillary. The leading electrolyte solution contained chloride (10 mM) as the leading anion and 10 mM acetate, pH 4.8 as the terminating electrolyte. As another example, a series of oligonucleotides with the amino group present at the 5' end and represented by the following sequences, i.e., MATGCATGCATGCAT (SEQ ID NO:1), (M)$_2$TCACGAGCGCTG (SEQ ID NO: 2), (M)$_3$ATTGGCCAGTC (SEQ ID NO: 3), (M)$_4$GGCCAATTGTC (SEQ ID NO: 4), and (M)$_5$TACTGATTA (SEQ ID NO: 5), where M is 2'fluoro-deoxycytidine nucleoside (dC$^F$), can be stacked by isotachophoresis in a 50 $\mu$m i.d. and 50 cm long capillary. The isotachophoresis can be performed with 5 mM caproic acid serving as the terminating electrolyte and 5 mM HCl adjusted to pH 3.9 with β-alanine serving as the leading electrolyte. Once a steady state is reached the surface can be exposed to light to bind the DNA sequences

Procedure 3

Method for Validating the Binding of Biomolecules to the Surface

The binding of DNA molecules to the surface can be evaluated as follows. Pressure inject into the capillary DNA molecules that are complementary to only one of the DNA's bound to the surface. The complementary DNA molecule should also have a fluorescence tag such that once this DNA hybridizes with that present on the surface the binding can be detected with the fluorescence. This procedure can be repeated for all the other strands of DNA suspected to be present. Once the binding has been evaluated the hybridized bound DNA molecules can be removed by raising the temperature and flushing out the molecules.

Another technique is atomic force microscopy that allows rapid, accurate and reproducible visualization of DNA absorbed onto the solid surface as described by Ye Fang et al in *Anal. Chem.* 1998, 70, 2123–2129. Scanning electron microscopy can also be used to detect the binding of DNA to the surface.

Applications of Binding Target Chemicals to Binder Chemicals

As previously described, specific target chemicals, such as nuclei acid sequences, can be positioned and affixed on a solid surface. Because of the availability of a large number of biomolecules that are different in structure and effective mobility many different such biomolecules can be positioned on different locations on a solid surface of channel. Furthermore, a plurality of channels can be arranged to be adjacent one another to provide a two dimensional arrangement of target chemicals in zones in these channels. For example, the zones in the channels can be arranged as a whole in a pattern in an overall shape of a square, rectangle, and the like. Such a capability in positioning target chemicals can be advantageously used in a wide range of applications.

Figure 3:
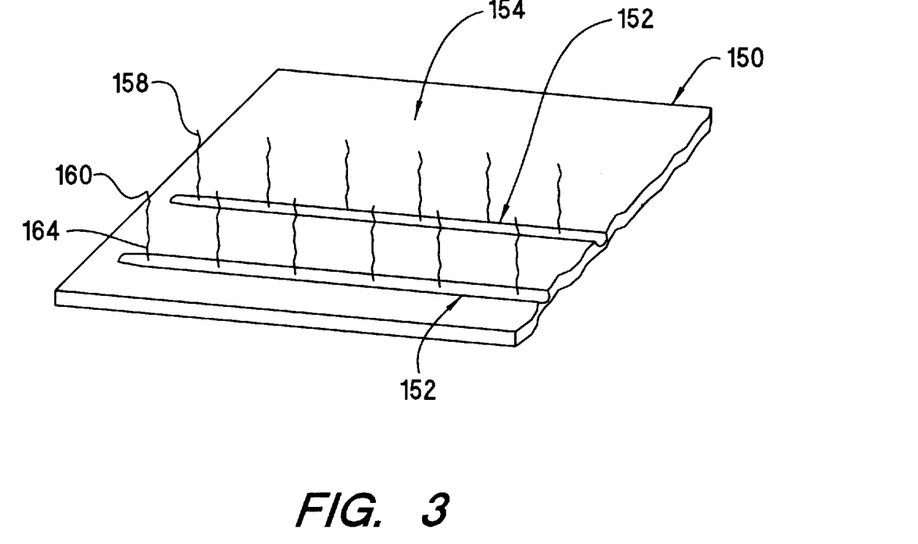
FIG. 3 shows an embodiment of an arrangement of multiple channels according to the present invention.

To make such two dimensional arrangements of zones and channels, one method is to start with a slate of substrate with a plurality of channels, perform isotachophoresis to arrange and affix binder chemicals onto zones along the channels, and split the slate into two halves to expose the channels, then bind the target chemicals on the binder chemicals and process further. The further process can involve performing chemical reaction, making structures such as electrical components (which will be described later), and the like. FIG. 3 shows an embodiment of an arrangement of such channels.

One example of an application is in a biosensor array. Briefly stated, such a biosensor array can be made with the target chemicals having a fluorescent marker, radioactive marker, or a labeled molecule that can be identified. When analyzing a sample, if a certain labeled target chemical is present, the labeled target chemical will bind to the corresponding binder chemical. By examining the fluorescent pattern in the two dimensional array of the zones present, and knowing what binder chemical locates in which zone in the channels, the presence of the target chemical can be confirmed. Techniques for labeling chemicals with suitable labels (radioactive, fluorescent, phosphorescent, etc.) and detecting such labels, particularly relating to biomolecules such as nucleic acid sequences, natural or synthetic DNA sequences, RNA sequences, and the like, are well known in the art. Examples of chromophores that can be used for attaching to biomolecules for detecting the biomolecules by light interaction, such as DNA sequences, include well known dyes such as: rhodamine T, rhodamine X, bodipy 1, bodipy 2, Texas red, fluorescein, Cy3, Cy5, and Lucifer yellow. For example, biosensor arrays and techniques of labeling and detecting biomolecules have been described by Stephen Fodor, J. L. Read, M. C. Pirrung, L. Stryer, Amy Tsai Liu, Dennis Solas, "Light directed spatially addressable parallel chemical synthesis," *Science,* 1991, 251, 767–773; and M. Chee, R. Yang, E. Hubbell, A. Bemo, X. C. Huang, D. Stem, J. Winkler, D. J. Lockhart, M. S. Morris, S. Fodor, Accessing genetic information with high density DNA arrays, *Science,* 1996, 274, 610–614, which descriptions are incorporated by reference herein. An interesting example of biosensor arrays are engineered RNA and DNA molecules that can be bound to the surface, and can act as molecular switches or communication modules. See, e.g., R. R. Breaker, *Protein Engineering,* 7, 1996, 442–448.

Len Adleman used a test tube full of DNA molecules with molecular biology techniques to solve the Hamiltonian path problem (also known as the "traveling salesman problem"). The computation was performed in solution by hybridization/ligation/PCR amplification of DNA elements, which were then separated by gel electrophoresis/affinity chromatography. See, Adleman, L. M., "Molecular Computation of Solutions to Combinatorial Problems," *Science,* 266, 1021, (1994). Although this experimental implementation of DNA computing was an important demonstration, the test tube methodology employed is not well suited for scale up to large combinatorial problems, involving as it does necessarily inefficient transfer and handing steps performed on a large scale, with macroscopic volumes and amounts of materials. With the present invention the travelling salesman problem can be solved with smaller amount of sample along with increased sensitivity and higher fidelity of information communication. The present technique involves anchoring a wide variety of nucleic acid sequences as an array on a two-dimensional surface and washing the solution containing all the possible combination of oligonucleotide sequences that represent the possible pathways of the traveling salesman over the array.

In the first step a series of zones each having the sequence representing the point of origin (vertex 0) can be stacked isotachophoretically and bound to the surface. This is followed by introducing a solution of DNA with sequences that are complementary with all other vertices in the Hamiltonian path as well as sequences that represent the edges connecting the vertices on the surface (there are seven vertices altogether including the origin in the path in the Adleman paper) on the surface. The sequences are subsequently exposed to DNA ligation reactions. This results in all possible combinations and sizes of DNA bound to the surface. In the next step all these sequences are cleaved from the surface using an enzyme that cuts at an appropriate place on the DNA sequence representing the origin vertex. This is followed by a size based capillary electrophoresis (CE) separation and collection of the fraction that contains all DNA's corresponding to seven sequences/vertices. In the next step the goal is to eliminate all sequences that have duplication, e.g., two of the same vertices present. This can again be performed on the surface, which now has sequences complimentary to only the seven vertices bound to the surface. The mixture that contains DNA's that are seven vertices long in length is exposed to the bound complimentary DNA representing the vertices in a sequential manner. For example in the first instance the mixture is exposed to a bound complimentary DNA representing the vertex zero. All the DNA molecules that have the sequence corresponding to the vertex zero (0) will bind to this zone and the rest are washed away. These DNA molecules are subjected to heat treatment and subsequently exposed to the next zone that has the sequence complimentary to vertex one (1) bound to the surface. This time the molecules that have the sequence of vertex one are bound to the other are washed away. So far all molecules that have sequences corresponding to vertex 0 and vertex 1 are selected. This process is continued till the DNAs that have all seven vertices have been selected thus providing a solution to the travelling salesman problem with seven vertices. With the present invention it is easy to extend the solution of the travelling salesman problem to more vertices where the processing can be performed in parallel on multiple chips thereby reducing the time required for complex algorithms.

Another example of a useful device that can be made using the present technique is a memory device that has an arrangement of memory units in read portals that can be read by appropriate optics. Techniques of forming and using DNA optical memory devices are described in WO 95/34890 by Heller et al., whose description is incorporated by reference herein. The present invention is particularly applicable in positioning a large number of DNA sequences (or RNA, nucleic acid sequences, or the like ) in the memory units. Briefly stated, in such a memory device, a DNA chromophoric memory unit has a DNA template. Chromophoric donors and chromophoric acceptors, which contain DNA segments complementary to segments of the template DNA, are attached to the template. The memory utilized energy transfer from the donor to the acceptor. In the presence of an active quencher, which permits non-radiation energy transfer, illumination to the donor does not result in radiation to a read detector via the acceptor. If the quencher is inactive, the chromophoric unit radiates to the read detector via the acceptor.

To write on the memory device, a photochemical reaction is used to destroy or inactive the quencher. Data are stored based on whether the quencher is active or not. Using the present invention, one can make a large number of such memory units in a very small area. The increase number of memory units significantly improves the amplification of the signal, which can easily be read by the read detector. On the DNA backbone, one can also put on different sequences, which will bind to different acceptors and donors, thus increasing the amount of information that can be stored. With a large number of DNA sequences with differences in the bases, the present invention is well-suited to position them in different locations on a solid surface. To make such a memory device, one component needed is the memory disk, which can be made by binding the DNA sequences (or nucleic acid sequence, etc.) on the disc surface. Such binding can be done using the above-described technique of isotachophoresis on a plurality of channels. To arrange the channels on a round disk, the channels can be formed as concentric circular channels.

One particularly beneficial application of the present invention is the ability to make very small molecular size structures with electrical property. In the effort to build smaller and smaller electrical devices, for example, in circuitry in computers or other electronic devices, such a capacity can be advantageously utilized. Reports of forming very small conductive wires and electronic components have been published. By positioning molecules, such as biomolecules (e.g., nuclei acid sequences) in known positions using the isotachophoresis technique of the present invention, one can form micrometer scale (and even nanometer scale) conductive wires and electronic components. Conductive wires of less than 1 micron in diameter can be formed. Braun et al., "DNA-templated assembly and electrode attachment of a conducting silver wire," *Nature,* 391, 775 (1998) describe the formation of DNA bridges between two points and chemically depositing silver on the DNA bridge such that a silver wire is formed. They construct two different anchoring oligonucleotides, each of which have disulfide group at their ends. The oligonucleotides are bound to two electrodes. Then a bridge is formed between the oligonucleotides and silver is deposited thereon. The Braun et al. disclosure of the formation of their conductive wire is incorporated by reference herein. Polymers can be connected to metallic patches. For example, Braun et al., supra, describe gold electrodes from which the silver wire derived from a DNA bridge can be formed. Silver is deposited on the DNA through silver-sodium ion exchange and formation of complexes between the silver and the DNA bases. For reference on silver-sodium exchange see, e.g., Barton, J. K., in *Bioinorganic Chemistry* (eds. Bertini, I. Et al.), Ch. 8 (University Science Books, Mill Valley, 1994). For reference on formation of complexes between silver and DNA see Spiro, T. G. (ed.) *Nucleic Acid-Metal ion Interactions* (Wiley Interscience, New York, 1980), Marzilli, L. G. et al., *J. Am. Chem. Soc.,* 99, 2797–2798 (1977). The disclosures of these references are incorporated by reference herein.) Techniques have also been developed to attach DNA to gold particles and assemble into supramolecular structures. See, Mirkin, et al., *Nature,* 382, 607 (1996), said disclosure is incorporated by reference herein. Such wires can be used to connect to electronic components such as resistors, transistors, etc.

Recently, it has been reported that electrically conductive oligonucleotides are formed on electrodes. See, "instant DNA Detection," *Chemical and Engineering News,* p. 47, May 25, (1998). Such electrically conductive oligonucleotides can be used to connect to electrically conductive wires or other electronic components made with DNA sequences positioned by techniques of the present invention. Other molecules that conduct electricity have also been made. See, *Chemical and Engineering News,* p. 7, Mar. 25, (1996). It has also been found that certain molecules behave like a logic gate and some molecules behave like transistors. See, *Chemical and Engineering News,* p. 57–62, Apr. 20, (1998). Other reports of molecular logic devices include A. Aviran and M. Ratner, *Chem. Phys. Lett.* 29, 277 (1974) and M. C. Petty, M. R. Bryce, D. Bloor, Eds. *Introduction to Molecular Electronics,* (Edward Arnold, London, 1995). One can connect such molecular transistors and logic devices to electrical wires made at positions arranged by utilizing the present isotachophoresis technique.

Procedure 4

Making Very Small Electrically Conductive Wires

To render a strand of nucleic acid sequences electrically conductive, one can apply the technique of metal deposition as described by Braun, et al., *Nature,* 391, 775, (1998). The bound strands can be converted to a DNA carrying silver beads for conduction. Being a polyanion, the DNA is loaded with silver ion by exchange of sodium ions with silver ions using 0.1 M silver nitrate basic aqueous solution. The silver ion DNA complex is reduced using basic hydroquinone solution (0.05 M ammonium hydroxide, pH 10.5) to form metallic silver aggregates bound to the DNA skeleton. The DNA templated wire is developed using an acidic solution (pH 3.5, citrate buffer) of hydroquinone (0.05 M) and silver ions (0.1 M) under low light conditions to give a silver wire along the DNA backbone.

Alternatively, DNA strands bound on a solid surface can act like pegs or posts to attract a gold microbead on which several DNA strands complementary to the bound DNA are present. This way conductive elements attached to the gold microbeads and be anchored. For references on binding gold to organic molecules, see, Mark Reed et al., *Science,* 278, 252–254 and Mirkin, et al., *Nature,* 382, 607 (1996), which disclosures are incorporated by reference herein. The conduction can now takes place through the molecular wire or a silver coated DNA strand that acts as a wire. On the other hand, it is not necessary for the DNA strands bound on the surface to have silver or gold deposited on the strand. The conduction of the bound strand may take place by virtue of the presence of a modified base that is charged or by movement of electrons through a conjugated organic structure.

The power of isotachophoresis as a technique for making a two dimensional arrangement of zones, for example, for application as an electronic device (such as an integrated circuit for computing) can be realized when one considers the fact that $10^5$ zones each containing $10^3$ molecules can be focused in one run on a 10 cm long CE capillary. Further, more than one event is carried out in parallel in $10^3$ multiple capillaries/parallel channels. Such techniques are not difficult since capillary arrays have been extensively used in DNA sequencing in the biotechnology industry. Thus, having $10^{11}$ molecules, if one performs 1 cycle in 10 min, in 1 minute one will processed $10^{10}$ molecules/events. Such a device, which basically provides zones of DNA 100 nanometers wide, will find application for building supra molecular circuits where DNA would be used to scaffold nano-size elements ("nanostructures") like molecular wires and transistors for the purpose of circuit building. Such nanostructures can then find utility as biosensors or lead to the production of application specific devices. Such a device can be used for the purpose of bio-computation by performing biochemical processes that copy, edit, replace and amplify DNA sequences in situ in consecutive cycles. The importance of capillary electrophoresis can be realized in the separation of the second generation fragments. An example of a device with a multitude of electrical conductive wires is shown in FIG. 3. Such electrical conductive wires can be made by binding nucleic acid sequences on solid surface at zones in channels in accordance with the present invention and deposit silver on the nucleic acid sequences with the techniques of Braun et al., supra. In FIG. 3 a silica substrate 150 has channels 152 on its surface 154. On the channel surface are a plurality of electrically conductive wires 158 with silver deposit 160 on nucleic acid sequence strand 164.

Figure 4:
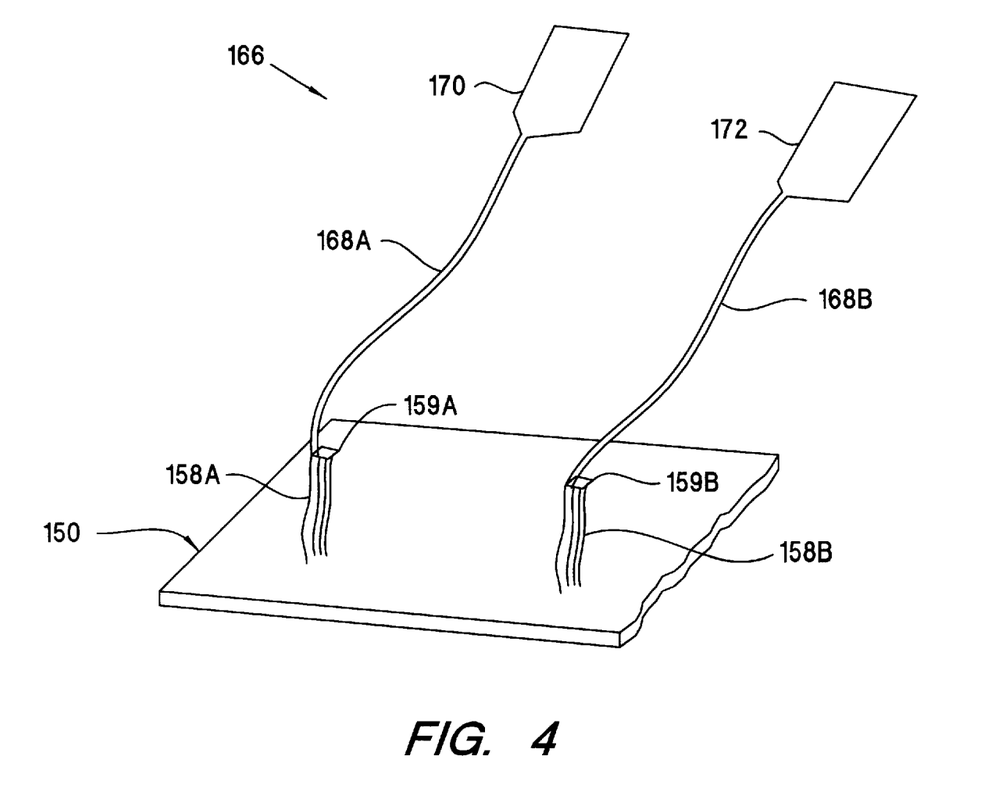
FIG. 4 shows an embodiment of an electrical device having electrically conductive wires according to the present invention.

FIG. 4 shows an embodiment of an electrical device 166 having electrically conductive wires 158A and 158B formed from biomolecules (e.g., nucleic acid sequence) according to the present invention on a substrate 150. The electrically conductive wires 158A are connected to an electrode 159A (which can be made of silver or gold). The electrode 159A is in turn connected by a wire 168A to an electrical component, which can be a transistor, resistor, capacitor, etc. Similarly, the electrically conductive wires 158B are connected to an electrode 159B to electrical component 172. Although not shown in FIG. 4, electrical connections can be made from the electrodes 159A, 159B, and from the electrical components 170, 172 to other electrical components, electrodes, and the like.

Although the illustrative embodiments of the device of the present invention and the method of using the device have been described in detail, it is to be understood that the above-described embodiments can be modified by one skilled in the art, especially in sizes and shapes and combination of various described features, without departing from the scope of the invention.

What is claimed is:

1. A method for binding chemicals on a wall surface of a channel, comprising:
   (a) introducing into the channel a first ionic species, a second ionic species and at least one solution having a plurality of chemicals, wherein under a given electric field the first ionic species has ions with higher effective mobility than the chemicals, and the second ionic species has ions with lower effective mobility than the chemicals;
   (b) applying an electrical potential difference between the two ends of the channel to separate the plurality of chemicals in the solution into spatial zones; and
   (c) binding a plurality of the chemicals to the wall surface after the zones have achieved a substantially steady state speed of migration in the channel.

2. A method according to claim 1 further comprising introducing a first electrolyte containing the first ionic species, and a second electrolyte containing the second ionic species into the channel, and interposing the at least one solution between said first and second electrolytes.

3. A method according to claim 1 further comprising binding a spacer on the wall surface of the channel prior to separating the chemicals in the solution in the channel, for binding the chemicals to the wall surface.

4. A method according to claim 1 wherein all the zones in the solution are connected in series and the series of zones is capped at one end by a zone of the ions of the first ionic species and at another end by a zone of the second ionic species and the chemicals are bound to the wall surface after the zones have achieved a steady state speed of migration in the channel.

5. A method according to claim 1 wherein each zone at steady state speed has substantially only one chemical species.

6. A method according to claim 5 wherein the chemicals include oligomers of monomers, said oligomers having selective affinity for partners.

7. A method according to claim 6 wherein the chemicals include oligonucleotides.

8. A method according to claim 7 wherein the oligonucleotides include charged bases.

9. A method according to claim 6 wherein the chemicals include polypeptides having selective affinity for partners.

10. A method according to claim 6 wherein the selective affinity comprises complementarity to other oligomers.

11. A method according to claim 5 wherein the chemicals include oligonucleotides, the oligonucleotides being selected from the group consisting of DNA, RNA, PNA, nucleosides linked by analogs of phosphodiester linkages, and a combination thereof.

12. A method according to claim 1 wherein a spatial zone of 10 microns or less in zone width is produced.

13. A method according to claim 3 wherein the at least some of the chemicals are stopped from further migration along the channel by rapid fixation on the channel surface.

14. A method according to claim 3 wherein the spacer is bound to the wall surface covalently.

15. A method according to claim 14 wherein the spacer is bound to the chemicals of the zones covalently and the binding is caused by photoreaction.

16. A method according to claim 14 wherein the spacer is bound to the chemicals of the zones covalently by means of a photoreactive azide group.

17. A method according to claim 14 wherein the wall surface has silanol group and the spacer is bound to the silanol group through reaction with a moiety selected from the group consisted of epoxy moiety, alkoxide moiety, and azide moiety.

18. A method according to claim 1 comprising separating the chemicals into at least 1,000 spatial zones of chemicals.

19. A method according to claim 1 comprising separating the chemicals into spatial zones of chemicals such that the majority of the zones each have a zone width of 10 microns or less.

20. A method of positioning a plurality of desired chemicals in ordered positions on a wall surface of a channel, comprising:

(a) binding the desired chemicals to affinity moieties to form targeting chemicals, each affinity moiety having affinity for its specific counterpart chemical;

(b) introducing into the channel a first ionic species, a second ionic species, and at least one solution having a plurality of the counterpart chemicals to the desired chemicals with affinity moieties, wherein under a given electric field the first ionic species has ions with higher effective mobility than the counterpart chemicals, and the second ionic species has ions with lower effective mobility than the counterpart chemicals;

(c) applying an electrical potential difference between the two ends of the channel to separate the plurality of counterpart chemicals in the solution into spatial zones;

(d) binding the counterpart chemicals to the wall surface; and (e) binding the targeting chemicals to their corresponding counterpart chemicals.

21. A method according to claim 20 further comprising introducing a first electrolyte containing the first ionic species and a second electrolyte containing the second ionic species into the channel, and interposing the at least one solution between said first and second electrolytes.

22. A method according to claim 20 further comprising binding a spacer on the wall surface of the channel prior to separating the counterpart chemicals in the channel, for binding the counterpart chemicals to the wall surface after the zones have been established.

23. A method according to claim 22 wherein all the zones are connected in series and the series is capped at one end by a zone of the ions of the first ionic species and at another end by a zone of the ions of the second ionic species and the binding of the counterpart chemicals to the wall surface occurs after the zones have achieved a steady state speed of migration in the channel.

24. A method according to claim 20 further comprising hybridizing at least a portion of the counterpart chemicals with matching oligomers in the targeting chemicals.

25. A method according to claim 24 wherein the matching oligomers include oligonucleotides.

26. A method according to claim 20 wherein the counterpart chemicals include oligonucleotides, the oligonucleotides being selected from the group consisting of DNA, RNA, PNA, nucleosides linked by analogs of phosphodiester linkages, and a combination thereof.

27. A method according to claim 20 further comprising connecting two or more of the counterpart chemicals together via molecular structures, wherein at least one of the molecular structures has a portion complementary to a portion of at least one of the connected counterpart chemicals.

28. A method according to claim 27, wherein at least one molecular structure connected to one of the counterpart chemicals is capable of conducting electricity.

29. A method according to claim 27 wherein the molecular structure is less than 1 micron in its smallest dimension.

30. A device for anchoring a plurality of chemical structures, comprising: a channel having an interior channel wall, the channel wall having a plurality of zones, each zone having a different species of binder chemical attached to the channel wall, wherein the binder chemical species are capable of binding a targeting chemical species and the zones are arranged in order of effective mobilities of the binder chemicals in a solution in a given electric field.

31. A device according to claim 30 wherein the species of binder molecules each have a portion complementing a corresponding portion in one of the targeting chemical species.

32. A device according to claim 30 wherein the majority of the zones each have a zone width of 10 microns or less.

33. A device according to claim 30 comprising more than 10,000 zones.

34. A device according to claim 30, wherein the targeting chemical species comprise oligonucleotides.

35. A device according to claim 34, wherein the oligonucleotides are selected from the group consisting of DNA, RNA, PNA nucleosides linked by analogs of phosphodiester linkages, and combinations thereof.

36. A device according to claim 30 further comprising secondary molecular structures immobilized on the binder chemical species via target chemical species that are bound to the binder chemical species, at least a portion of the secondary molecular structures being connected to other secondary molecular structures immobilized on the binder chemical species.

37. A device according to claim 36 wherein at least some of the secondary molecular structures can conduct electricity.

38. A device according to claim 37, wherein at least some of the secondary molecular structures are connected to enable electrical communication with electrical components.

39. A device according to claim 30 further comprising a plurality of channels each having binder chemical species.

40. An electrical device, comprising: a substrate having a two-dimensional arrangement of a plurality of zones, wherein within in each zone the substrate is attached to a different molecular structure comprised of a binder species coupled to an electrically conductive component and further wherein the binder species is capable of coupling to a target species and the zones are arranged in order of effective mobilities of the target species in a solution in a given electric field.

* * * * *